United States Patent [19]

Edwards

[11] 4,361,585

[45] Nov. 30, 1982

[54] METHOD OF TREATMENT TO RELIEVE PAIN IN MUSCLES OR BONES

[76] Inventor: Roy Edwards, 1415 Highland Dr., Solana Beach, Calif. 92075

[21] Appl. No.: 258,662

[22] Filed: Apr. 29, 1981

Related U.S. Application Data

[63] Continuation-in-part of Ser. No. 193,147, Oct. 2, 1980, abandoned, which is a continuation-in-part of Ser. No. 35,604, May 3, 1979, Pat. No. 4,239,781, which is a continuation of Ser. No. 876,203, Feb. 9, 1978, abandoned.

[51] Int. Cl.³ .............................................. A61K 31/08
[52] U.S. Cl. ................................................... 424/342
[58] Field of Search ......................................... 424/342

[56] References Cited

U.S. PATENT DOCUMENTS

| | | | |
|---|---|---|---|
| 2,801,201 | 7/1957 | Kipnis | 424/310 X |
| 2,843,621 | 7/1958 | Oroshnik et al. | 426/310 X |
| 4,239,781 | 12/1980 | Edwards | 424/342 |

OTHER PUBLICATIONS

York et al., Chemical Abstracts 84:169611v, (1976).
Zecchi et al., Chemical Abstracts 82:77057z, (1975).
Handbook of Nonprescription Drugs, 5th ed., 1977, pp. 289-295.

*Primary Examiner*—Leonard Schenkman
*Attorney, Agent, or Firm*—McDougall, Hersh & Scott

[57] ABSTRACT

Treatment of muscle or bone ailments to relieve pain by topical application of fluid polyalkylene glycol.

9 Claims, No Drawings

METHOD OF TREATMENT TO RELIEVE PAIN IN MUSCLES OR BONES

This is a continuation-in-part of my copending application Ser. No. 193,147, filed Oct. 2, 1980, now abandoned as a continuation-in-part of application Ser. No. 35,604, filed May 3, 1979 (now U.S. Pat. No. 4,239,781, issued Dec. 16, 1980), as a continuation of application Ser. No. 876,203, filed Feb. 9, 1978, now abandoned.

This invention relates to topical application for treatment in the relief of pain from muscular or bone ailments, such as arthritis, bursitis and the like.

In my aforementioned issued U.S. Pat. No. 4,239,781, description is made of the discovery that such skin ailments as flaking, athlete's foot and eczema could be treated successfully by the topical application of a composition, the active ingredient of which consists essentially of polyethylene glycol. It was subsequently found, as described and claimed in my aforementioned copending application Ser. No. 193,147, that polyethylene glycol was also effective in the treatment of skin burns by the topical application of the polyethylene glycol to the burned areas of the skin.

It has now been found, and this finding is completely unexpected, that polyethylene glycol has a very desirable effect in alleviating the pain of arthritis, bursitis and other ailments of the joints, bones and muscle, when polyethylene glycol is topically applied to wet the area immediately adjacent the affected area and maintained thereon for an extended period of time.

In the case of arthritis or bursitis, this can be accomplished with an absorbent pad applied to the affected area and impregnated with polyethylene glycol either before application of the pad or by impregnation afterwards. Such pad can be wrapped about the infected area or taped or otherwise adhered to the affected area during the period of treatment.

Instead of making use of an absorbent pad wrapped about or adhered to the affected area, use can be made of a glove of absorbent material that can be worn on the hand in the event that the painful area is in the hand or one or more of the fingers. It can be provided in the form of a sleeve of absorbent material which can be drawn over the arm or foot or joint for treatment by wetting with the polyethylene glycol. Instead it can be provided in the form of a stocking, skull cap or the like to be worn on the affected area.

It will be apparent that the polyethylene glycol for use in the practice of this invention should comprise a polyethylene glycol of fluid consistency, such as a polyethylene glycol having a molecular weight within the range of 2-1000, but polyethylene glycol of higher molecular weight can be used when reduced to fluid consistency by solution in a suitable solvent or diluent which is inert from the standpoint of skin irritation or effect. Suitable diluents include water, ethylene glycol and propylene glycol mononers or other alcohols and such diluents may be used in amounts to constitute up to 50% by weight of the treating composition.

Instead, use can be made of other polyalkylene glycols of low molecular weight such as polypropylene glycol, polybutylene glycol and the like within the molecular weight range of 200-10,000 and preferably within the range of 200-800. Such polyalkylene glycols are marketed by Carbide Chemical Corporation, New York City, New York under the trade name Carbowax.

For use in accordance with the practice of this invention, it is preferred to make use of the polyethylene glycol or polyalkylene glycol without dilution with other materials or solvents although adjuvants such as surface active agents and their softening agents and saturated oils can be incorporated in amounts up to 5% by weight of the polyalkylene glycol.

The time factor for treatment is significant in that relief is obtained when the affected area is wet with the polyalkylene glycol over a period of time which may extend from a few minutes to hours until pain relief is experienced. Thereafter, infrequent treatment, at most, is desired to avoid return of pain. For the most part, relief continues over an extensive period of time to indefinitely.

The following examples are given by way of illustration but without limitation of the practice of the invention.

EXAMPLE 1

A cotton pad wet with polyethylene glycol (Carbowax 400) is applied to the shoulder pained with arthritis. The pad is held to the shoulder by a suitable gauze wrapping. Periodically (about once every 3 to 4 hours) additional amounts of polyethylene glycol are applied to maintain the pad in a wet state. After a number of hours, pain relief is experienced and substantially completely eliminated within about 24 hours, after which the pad can be removed. Relief will continue for a number of days or longer.

EXAMPLE 2

In the case of bursitis in the arm, a cotton sleeve is drawn onto the arm to cover the affected area. The sleeve is then impregnated with polyethylene glycol (Carbowax 200) and maintained on the arm for several hours, with occasional wetting with Carbowax 200, as required to keep the sleeve wet. The sleeve is worn for 6 to 24 hours for relief of pain.

EXAMPLE 3

Arthritis in the fingers or bursitis in the hand can be treated by wearing a glove on the hand and impregnating the glove with the following composition:
Carbowax 600—95% by weight
Vegetable oil—3% by weight
Methanol—2% by weight
The glove can be worn with occasional wetting with the composition until pain is relieved (about 12-24 hours).

An important concept is to maintain the liquid polyethylene glycol or other polyalkylene glycol in direct contact with the affected area over an extended period of time. Thus, while the invention has been described with reference to the use of an absorbent material as a carrier for the liquid polyethylene glycol or other polyalkylene glycol, where it is possible to enclose the area as in a glove, stocking, sleeve or the like, the preferred use is to make use of a support in the form of a fluid impervious material, such as rubber or plastic gloves, rubber or plastic sleeve and the like which retains the liquid glycol in direct contact completely to wet the area without the need for periodic replacement, rewetting or impregnation. With body ailments, for example, use can be made of a rubber or plastic belt wrapped around the affected area whereby the liquid glycol that is supplied to the affected area is retained over an extended period of time in wet contact with the area subject to treatment.

It will be apparent from the foregoing that I have provided a new and novel treatment for the relief of pain occasioned by ailments of the bone, muscles and joints which treatment can be carried out individually, in a safe and efficient manner.

It will be understood that changes may be made in the details of formulation and application without departing from the spirit of the invention, especially as defined in the following claims.

I claim:

1. A method of treatment to relieve pain from muscles or bone ailments comprising topically wetting the pained area with an effective amount of a fluid composition consisting essentially of polyalkylene glycol as the sole active ingredient until relief of pain is experienced.

2. A method as claimed in claim 1 in which the area immediately adjacent the affected area is covered with an absorbent material and which includes the step of maintaining the absorbent material wet with the polyalkylene glycol.

3. The method as claimed in claim 1 in which the polyalkylene glycol is polyethylene glycol.

4. The method as claimed in claim 2 in which the absorbent material is in the form of a pad.

5. The method as claimed in claim 2 in which the absorbent material is in the form of a glove to be worn on the hand.

6. The method as claimed in claim 2 in which the absorbent material is in the form of a shoulder pad.

7. The method as claimed in claim 2 in which the absorbent material is in the form of an arm band.

8. The method as claimed in claim 2 in which the absorbent material is in the form of a stocking.

9. The method as claimed in claim 1 in which the area wetted with the fluid polyalkylene glycol is covered with a fluid impervious support.

* * * * *